(12) United States Patent
McDaniel

(10) Patent No.: US 7,077,823 B2
(45) Date of Patent: Jul. 18, 2006

(54) BIDIRECTIONAL STEERABLE CATHETER WITH SLIDABLE MATED PULLER WIRES

(75) Inventor: Benjamin D. McDaniel, Corona Del Mar, CA (US)

(73) Assignee: Biosense Webster, Inc., Miami Lakes, FL (US)

( * ) Notice: Subject to any disclaimer, the term of this patent is extended or adjusted under 35 U.S.C. 154(b) by 44 days.

(21) Appl. No.: 10/716,822

(22) Filed: Nov. 19, 2003

(65) Prior Publication Data
US 2005/0107737 A1  May 19, 2005

(51) Int. Cl.
*A61M 37/00*  (2006.01)

(52) U.S. Cl. .................................. 604/95.01

(58) Field of Classification Search ............. 604/95.01, 604/95.02, 95.03, 95.04, 95.05, 280, 264; 606/41, 45, 49, 205–208; 607/122; 600/374, 600/131, 393, 139, 129, 146, 147
See application file for complete search history.

(56) References Cited

U.S. PATENT DOCUMENTS

| 3,058,473 | A | * | 10/1962 | Whitchead ............... 604/95.04 |
| 3,470,876 | A | * | 10/1969 | Barchilon ................ 604/95.04 |
| 5,199,950 | A | * | 4/1993 | Schmitt et al. ........... 604/95.04 |
| 5,395,327 | A | * | 3/1995 | Lundquist et al. .......... 604/528 |
| 5,531,686 | A |   | 7/1996 | Lundquist et al. |
| 5,676,653 | A |   | 10/1997 | Taylor et al. |
| 5,824,031 | A | * | 10/1998 | Cookston et al. ........... 607/122 |
| 5,882,333 | A |   | 3/1999 | Schaer et al. |
| 5,944,690 | A | * | 8/1999 | Falwell et al. ......... 604/170.03 |
| 6,132,390 | A |   | 10/2000 | Cookston et al. |
| 6,210,407 | B1 | * | 4/2001 | Webster ...................... 606/41 |
| 6,332,881 | B1 |   | 12/2001 | Carner et al. |
| 2002/0068867 | A1 |   | 6/2002 | Ameling et al. |

* cited by examiner

*Primary Examiner*—Manuel Mendez
(74) *Attorney, Agent, or Firm*—Christie, Parker & Hale, LLP

(57) ABSTRACT

An improved steerable catheter comprises an elongated tubular catheter body with a flexible tip section. A pair of slidably mated puller wires fixedly attached to each other at their distal ends extend from a handle at the proximal end of the catheter body through a lumen in the catheter body and into a lumen in the tip section. Proximal movement of one puller wire relative to the other results in deflection of the tip section.

19 Claims, 9 Drawing Sheets

BIDIRECTIONAL STEERABLE CATHETER WITH SLIDABLE MATED PULLER WIRES

FIELD OF THE INVENTION

The present invention relates to catheters having a steerable tip section and, more particularly, to an improved bidirectional steerable catheter.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., the femoral artery, and then guided into the chamber of the heart which is of concern. Within the heart, the ability to control the exact position and orientation of the catheter tip is critical and largely determines how useful the catheter is.

Steerable catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter to the side wall of the catheter shaft. In this arrangement, lengthwise movement of the piston relative to the housing results in deflection of the catheter tip section. The design described in U.S. Pat. No. RE 34,502 is generally limited to a catheter having a single puller wire.

Bidirectional steerable catheters are also generally well-known, as a variety of designs have been proposed. In many such designs, e.g., as described in U.S. Pat. Nos. 6,066,125, 6,123,699, 6,171,277, 6,183,463 and 6,198,974, all of which are incorporated herein by reference, a pair of puller wires extend through a lumen in the main portion of the catheter shaft and then into opposing off axis lumens in a deflectable tip section where the distal end of each puller wire is attached to the outer wall of the deflectable tip. Pulling one wire in a proximal direction causes the tip to deflect in the direction of the off axis lumen in which that wire is disposed.

In other designs, e.g., as described in U.S. Pat. No. 5,531,686, the puller wires are attached to opposite sides of a rectangular plate that is fixedly mounted at its proximal end and extends distally within a lumen in the tip section. In this arrangement, pulling one of the wires proximally causes the rectangular plate to bend in the direction of the side to which the pulled puller wire is attached, thereby causing the entire tip section to deflect.

In all of the designs for a steerable catheter, the puller wire or wires are attached at their distal ends to some structure in the tip section of the catheter. Such designs require time, effort and expense to make such attachments. It would be useful to provide a steerable tip catheter that does not require that the puller wires be fixedly attached to the catheter tip section.

SUMMARY OF THE INVENTION

The invention is directed to an improved steerable catheter, particularly a bidirectional steerable catheter. The catheter comprises an elongated, tubular catheter body having at least one lumen extending therethrough and a flexible tubular tip section having at least one lumen extending therethrough. The catheter body and tip sections may be a single structure or separate structure wherein the tip section is fixedly attached to the distal end of the catheter body. Whether by the use of a more flexible material for the tip section or the inclusion of a stiffening structure in the catheter body, the tip section is more flexible than the catheter body.

The catheter further comprises first and second puller wires having proximal and distal ends. Each puller wire extends from a control handle at the proximal end of the catheter body through a lumen in the catheter body and into a lumen in the tip section. Along the length of the portion of the puller wires that extend through the catheter body and tip section, the puller wires are slidably mated. As usual herein, "mated" means that the puller wires are maintained in a closely adjacent relationship. Such a relationship can be maintained by an arrangement wherein the puller wires have an interlocking relationship with each other. Alternatively, the puller wires may be disposed in a tubular sleeve dimensioned so as to maintain the puller wires in close adjacent relationship. The distal ends of the puller wires are fixedly attached to each other.

Proximal movement of the thumb control relative to the handle housing results in proximal movement of the first piston and first puller wire relative to the handle housing and catheter body, which results in deflection of the tip section in the direction of the lumen into which the first puller wire extends. Distal movement of the thumb control relative to the handle housing results in distal movement of the first piston, causing proximal movement of the second piston and puller wire relative to the handle housing and catheter body, which results in deflection of the tip section in the direction of the lumen into which the second puller wire extends.

The control handle comprises means for pulling at least one of the puller wires in a proximal direction and preferably, means for pulling one puller wire in a proximal direction while simultaneously pushing the other puller wire in a distal direction. A particularly preferred handle comprises one or more generally circular gears having teeth that engage teeth along a proximal portion of the puller wires or to engage teeth along a bar or rod to which each puller wire is attached. The gear or gears are arranged so that by rotation of the one gear or one of a plurality of gears causes the first and second puller wires to move in opposite directions, one proximally and the other distally. As a result, the tip section deflects in the direction of the puller wire that moves proximally.

DESCRIPTION OF THE DRAWINGS

These and other features of the advantages of the present invention will be better understood by reference to the following detailed description when considered in conjunction with the accompanying drawings wherein.

DETAILED DESCRIPTION OF THE INVENTION

Figure 1:
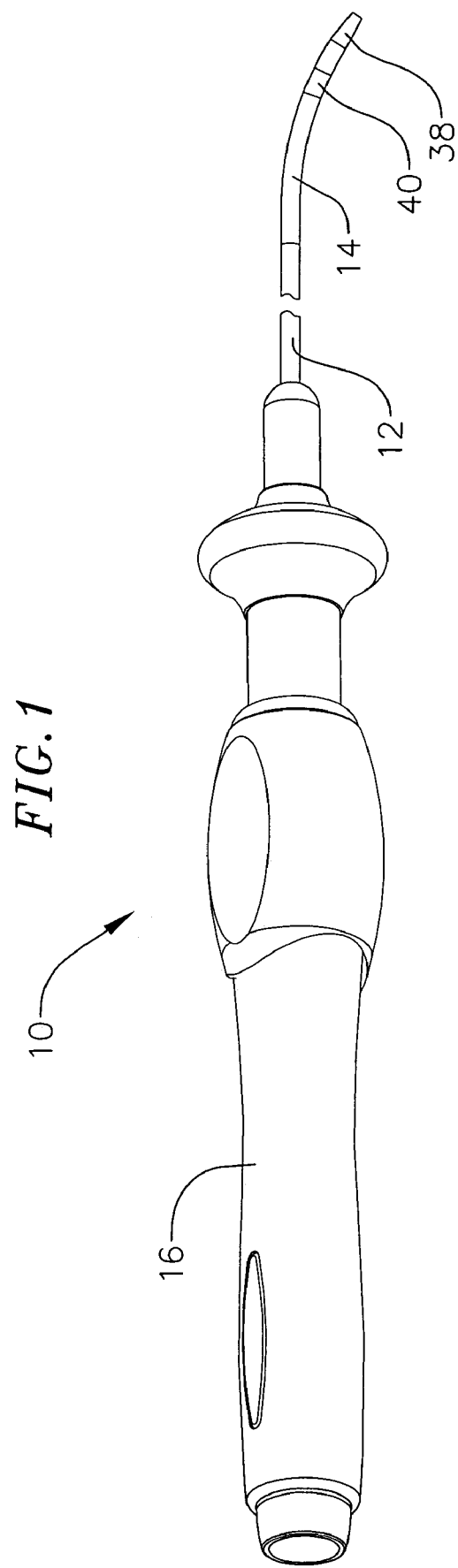
FIG. 1 is a side view of an embodiment of the catheter of the invention.

In a particularly preferred embodiment of the invention, there is provided a steerable bidirectional electrode catheter. As shown in FIG. 1, a preferred catheter comprises an elongated catheter body 10 having a proximal section 12, a distal tip section 14, and a control handle 16 at the proximal end of the proximal section 12.

Figure 2:
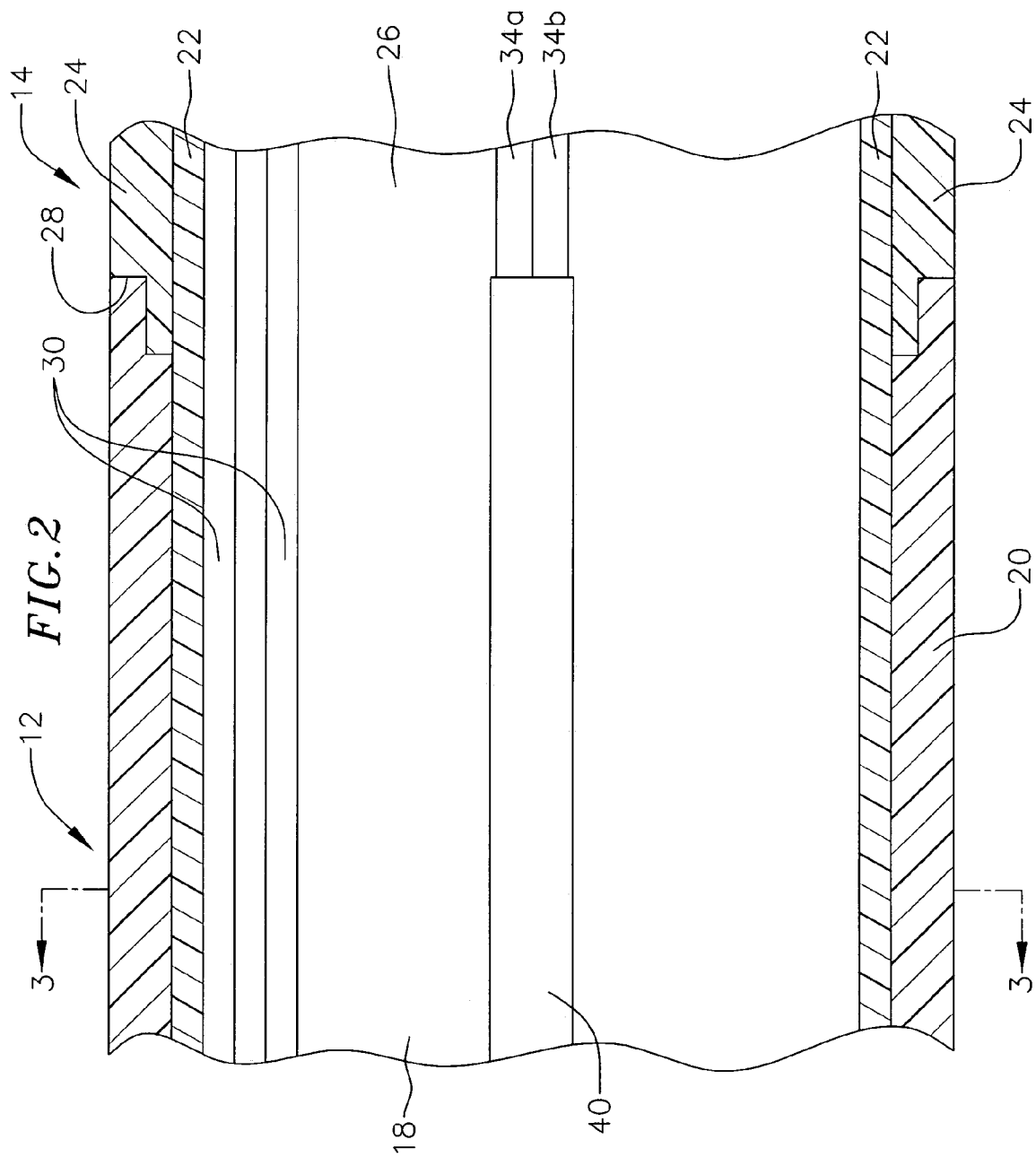
FIG. 2 is a side cross-sectional view of the junction of the proximal section and tip section of an embodiment of a catheter according to the invention.
Figure 3:
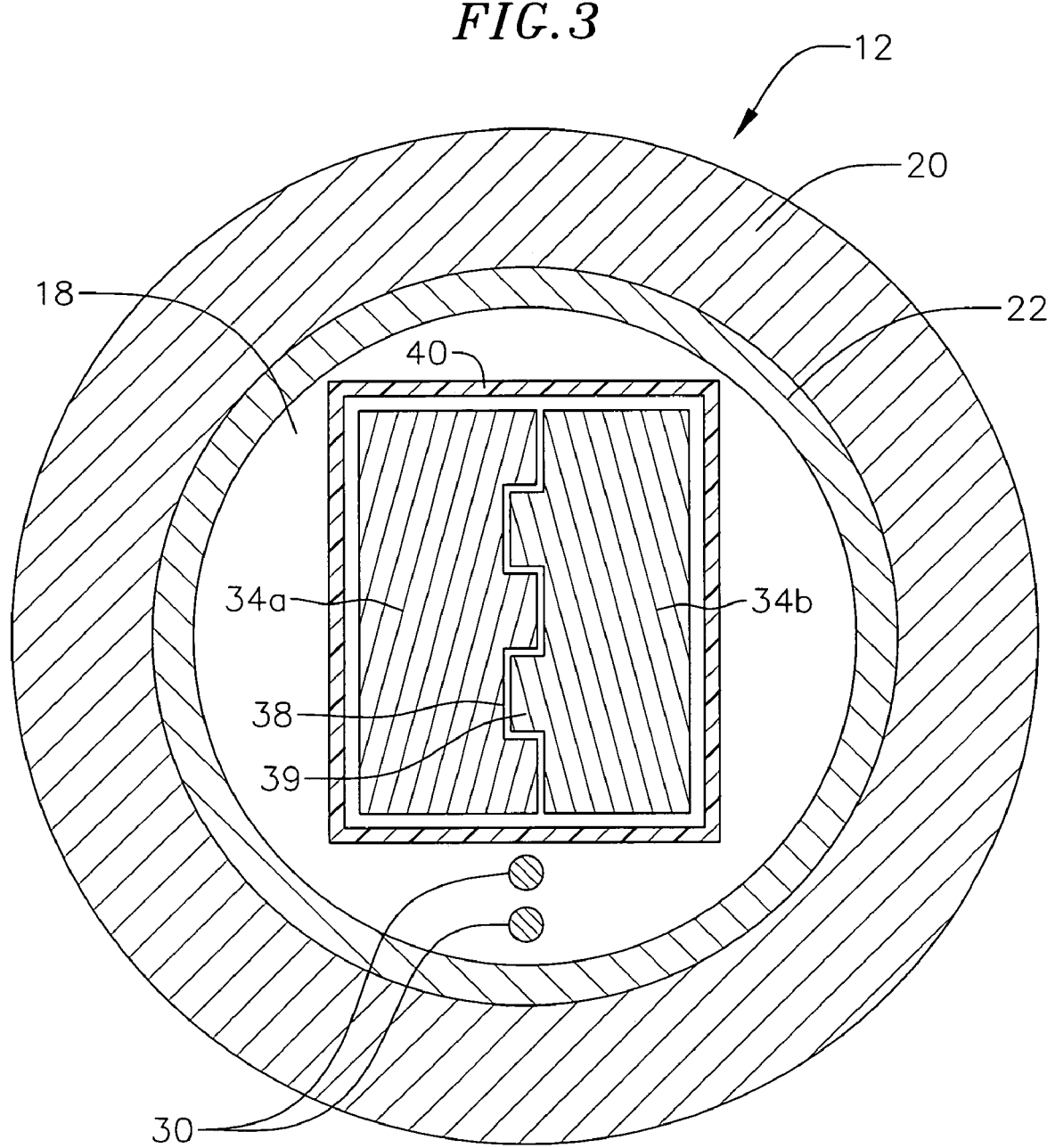
FIG. 3 is a transverse cross-sectional view of the proximal section shown in FIG. 2 taken along line 3—3.

As shown in FIGS. 2 and 3, the proximal section 12 comprises an elongated tubular construction having a single axial or central lumen 18. The proximal section 12 is flexible, i.e., bendable, but substantially non-compressible along its length. The proximal section 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the proximal section 12 so that when the control handle 16 is rotated the tip section 14 will rotate in a corresponding manner.

The overall length and diameter of the catheter may vary according to the application. A presently preferred catheter has an overall length ranging from about 90 to about 120 cm, more preferably from about 100 to 110 cm. The outer diameter of the proximal section 12 is not critical, but is preferably no more than about 8 French. The inner surface of the outer wall 20 may optionally be lined with a stiffening tube 22 as described in more detail in U.S. Pat. No. 5,897,529, the disclosure of which is incorporated herein by reference. The stiffening tube 22 may be made of any suitable material, but preferably is made of polyimide or nylon. The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a central lumen 18 diameter of about 0.052 inch. The stiffening tube 22 is optional and may be omitted.

Figure 4:
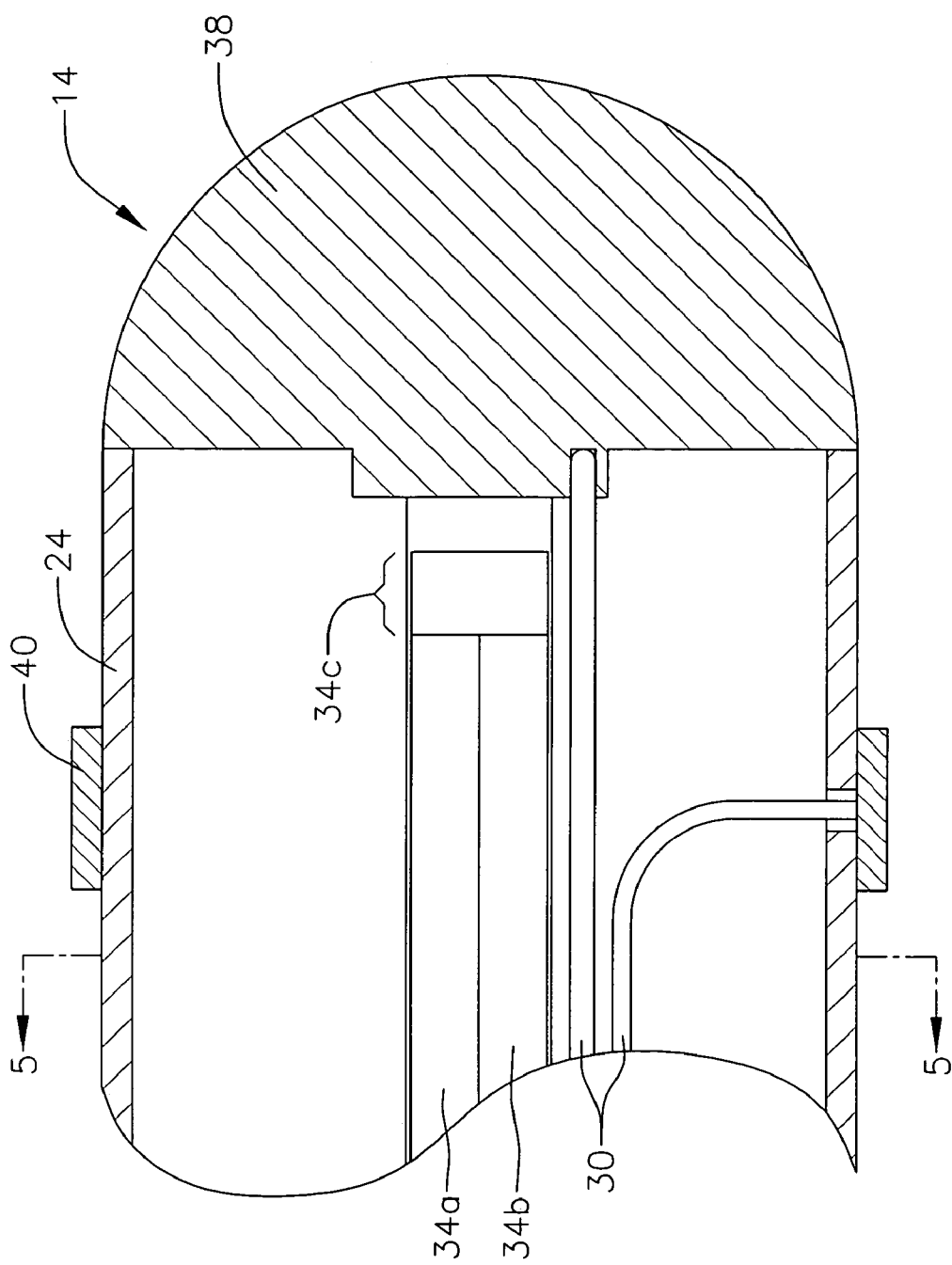
FIG. 4 is a side cross-sectional view of the distal end of the tip section shown in FIG. 2.
Figure 5:
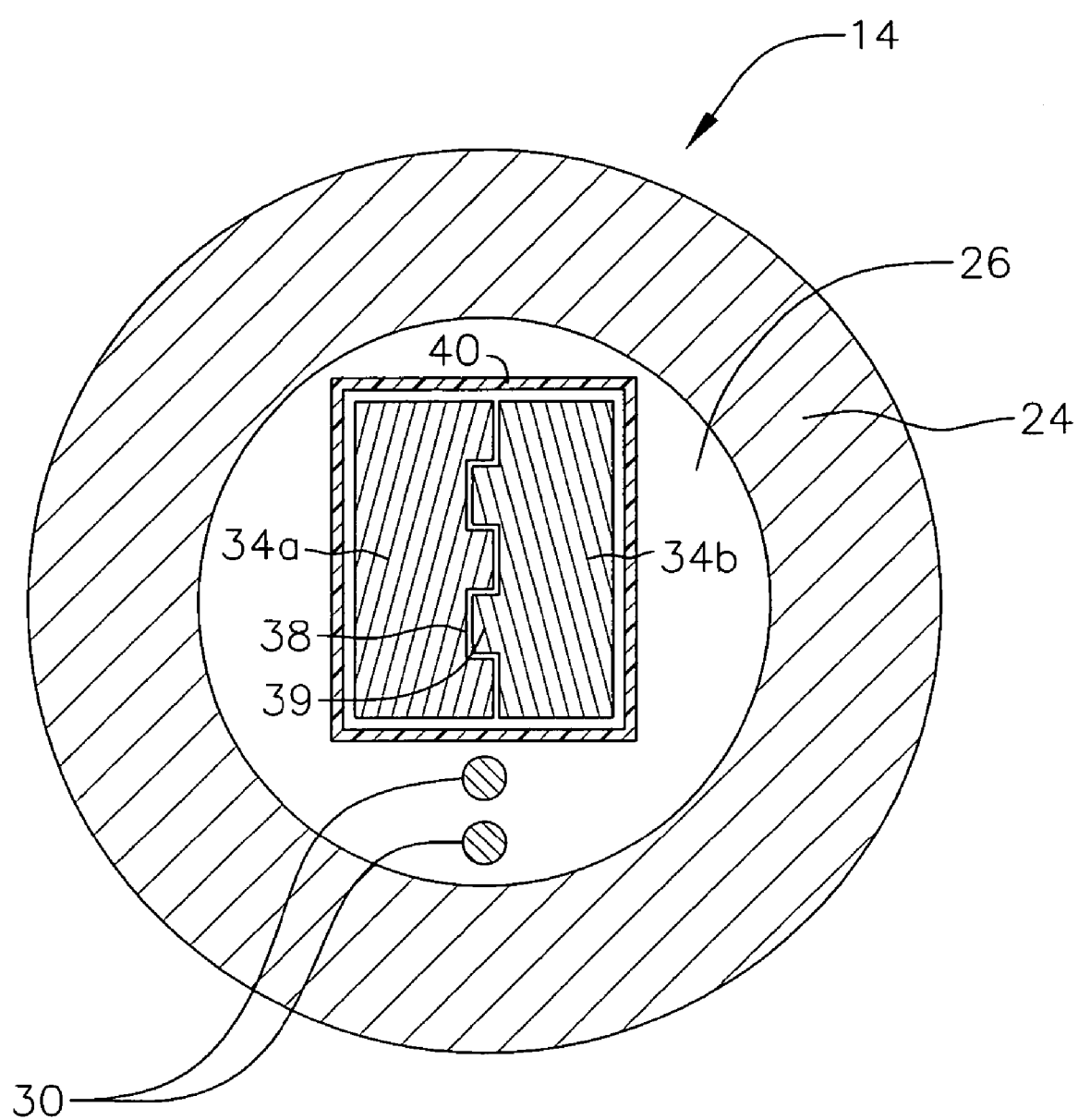
FIG. 5 is a transverse cross-sectional view of the tip section shown in FIG. 4 taken along line 5—5.

As shown in FIGS. 4 and 5, the tip section 14 comprises a short section of flexible tubing 24 having a single lumen 26 extending therethrough, although additional lumens can be included if desired. The flexible tubing 24 is made of a suitable non-toxic material that is more flexible than the proximal section 12. A presently preferred material for the tubing 24 is polyurethane. The outer diameter of the tip section 14, like that of the proximal section 12, is preferably no greater than about 8 French, more preferably about 6½ French or less.

In the embodiment shown, the tip section 14 and the proximal section 12 are separate structures that have been fixedly attached to each other. It is understood that the tip section 14 and proximal section 12 could be formed as a unitary structure as desired. To attach the tip section 14 to the proximal section 12, the proximal end of the tip section 14 comprises an outer circumferential notch 28 that is received in a corresponding inner circumferential notch 29 at the distal end of the proximal section 12. The tip section 14 and proximal section 12 may be attached by glue or the like.

As shown in FIG. 4, the tip section 14 carries a tip electrode 38 and a ring electrode 40. The length of the tip electrode 38 is not critical and will depend on the desired application for which the catheter is to be used. Preferably the tip electrode 38 has an exposed length ranging from about 2 mm to about 6 mm. Mounted along the length of the tip section 14 is ring electrode 40. The length of the ring electrode 40 similarly is not critical, but preferably ranges from about 0.5 mm to about 3 mm. Additional ring electrodes can be provided if desired. If multiple ring electrodes are used, they are spaced apart in any fashion as desired so long as their edges do not touch.

The tip electrode 38 and ring electrode 40 are each electrically connected to a separate lead wire 30. Each lead wire 30 extends through the lumen 26 in the tip section 14 and the central lumen 18 in the proximal section 12 and into the control handle 16. The proximal end of each lead wire 30 is connected to an appropriate connector (not shown), which can be plugged into or otherwise connected to a suitable monitor, source of energy, etc., within or outside the control handle 16.

To deflect the tip section 14, there is provided a pair of puller wires 34a and 34b that extend through the catheter body 12 and into the tip section 14. The puller wires 34 are made of any suitable metal, such as stainless steel or Nitinol. Preferably each puller wire 34 has a lubricious coating of, e.g., Teflon® or the like. Each puller wire 34 extends from the control handle 16, through the central lumen 18 in the proximal section 12 of the catheter body and into the lumen 26 of the tip section 14. At least the portions of the puller wires that extend through the proximal section 12 and tip section 14 are slidably mated to each other. At their distal ends, the two puller wires 34a and 34b are fixedly attached to each other at a joint 34c by soldering, welding or the like. The puller wires 34 can have any desired cross-sectional shape, e.g., round, rectangular, etc. Further, the cross-sectional shape of the first puller wire 34a need not be the same as that of the second puller wire 34b.

Figure 6:
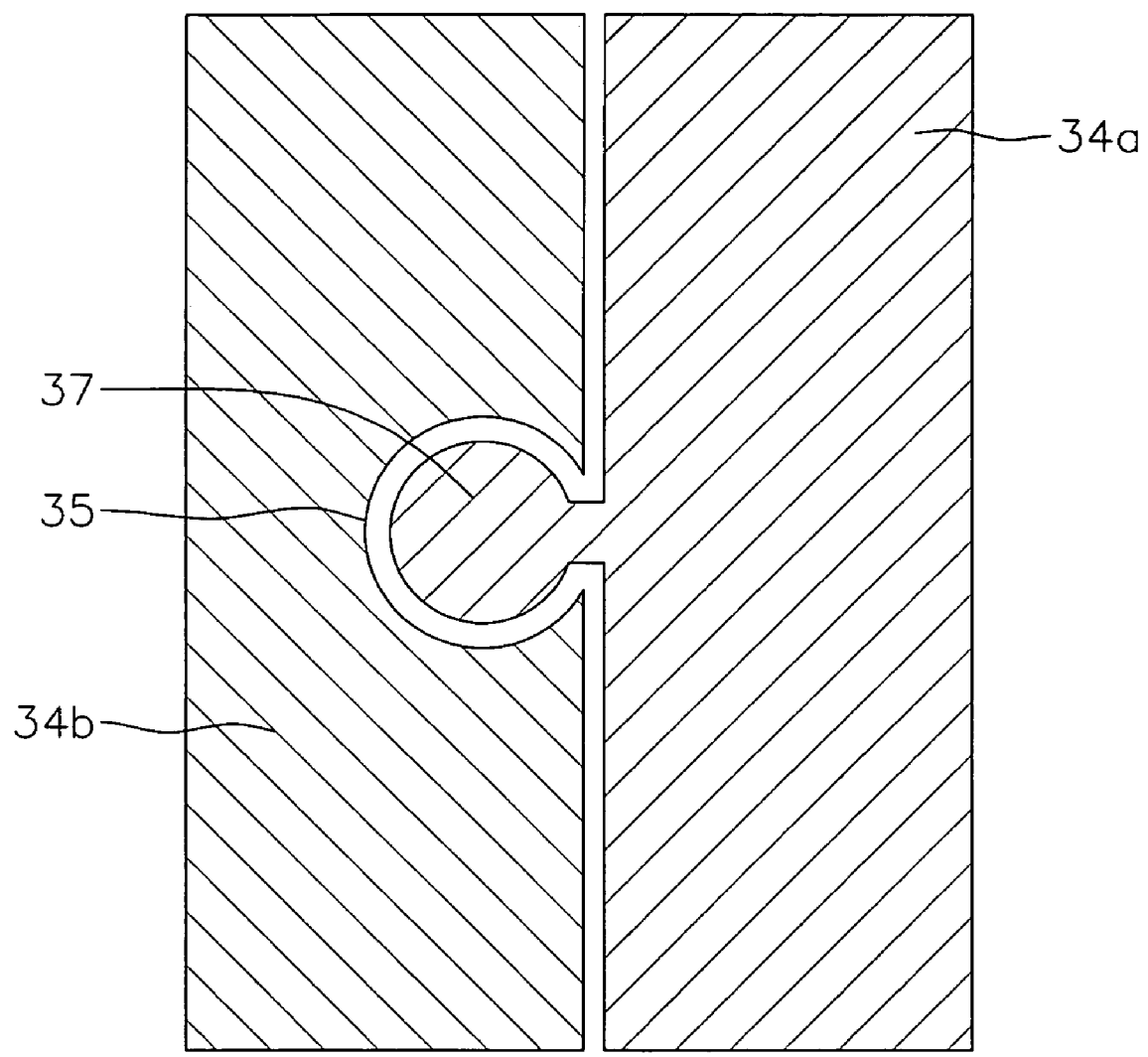
FIG. 6 is a side cross-sectional view of one embodiment of an interlocking puller wire pair according to the invention.

There are several ways in which the puller wires can be mated along their length. For example, in one embodiment, as shown in FIG. 6, the puller wires 34a and 34b are interlocked. In this embodiment, puller wires 34a and 34b are both rectangular in cross-sectional shape. The first puller wire 34a has a generally circular notch 35 along its length extending inwardly from the surface facing the second puller wire 34b. The second puller wire 34b comprises a rib 37 having a generally circular cross-section that extends outwardly from the surface facing the first puller wire 34a and into notch 35. Notch 35 and rib 37 are sized to allow the first and second puller wires to slide freely relative to each other, but to prevent the puller wires from separating.

Figure 7:
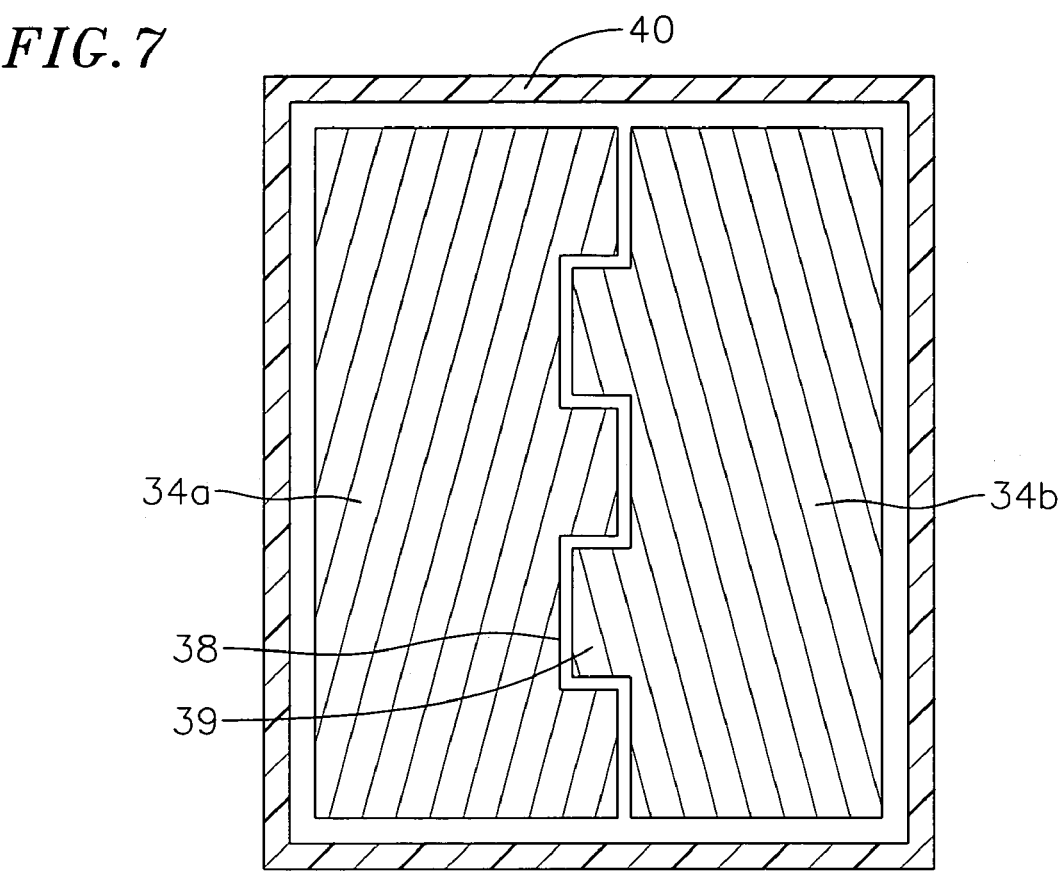
FIG. 7 is a side cross-sectional view of another embodiment of a mated puller wire pair according to the invention.

In another preferred embodiment, as shown in FIG. 7, rectangular puller wire 34a has a pair of generally rectangular notches 38 that receive mating rectangular ribs 39 of puller wire 34b. In this embodiment, because the puller wires are not interlocking, a tube or sleeve 40 is provided that surrounds the puller wires to keep them in a closely adjacent relationship. The sleeve 40 may be made of any suitable material, e.g., polyimide or polyurethane or may take the form of a compression coil. The sleeve 40 may be of any appropriate shape, e.g., rectangular, as shown. The sleeve 40 preferably extends the full length of the portion of the puller wires 34 within the catheter body and may extend into the handle. The composition of the sleeve 40 may be consistent throughout or may vary. For example, a stiff sleeve, e.g., made of polyimide, may surround the puller wires throughout the proximal section 12 of the catheter body and a more flexible sleeve, e.g., made of polyurethane, may surround the puller wires 34 in the tip section 14. Rather than a sleeve, the puller wires 34 may extend through a lumen in the proximal section of the catheter body and/or the catheter tip section that has a size and shape that maintains the puller wires 34 in close adjacent relation. It is understood that the puller wires 34a and 34b could be disposed within a sleeve in the proximal section 12 of the catheter body 10 and then extend into a lumen in the tip section that is sized and shaped to maintain the close relationship of the puller wires.

Figure 8:
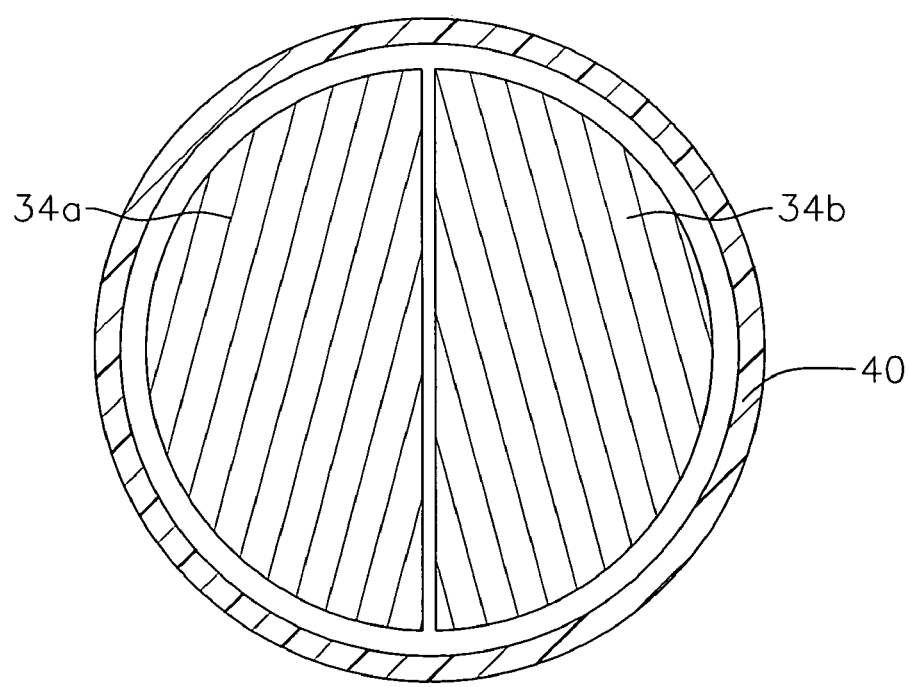
FIG. 8 is a side cross-sectional view of another mated puller wire pair according to the invention.

With reference to FIG. 8, there is shown yet another exemplary embodiment of a mated puller wire pair. In this embodiment, the puller wires 34a and 34b are both semi-circular in cross-section and are maintained in close adjacent relation by a generally circular sleeve 40.

As can be seen, the cross-sectional shape of the puller wires can vary as desired. Preferably, the shape of the puller wires is selected to promote deflection of the tip section in a single plane. In this regard, puller wires having a generally rectangular cross-section or at least one flat longitudinal surface are preferred. Alternatively or additionally, the cross-section of configuration of the sleeve can be chosen to promote deflection in a single plane. By using a sleeve having a rectangular or oval cross-sectional configuration, puller wires having a circular cross-sectional shape (or other shape that does not promote deflection of the tip section in a single plane) can be used and still result in a deflection generally within a single plane.

The puller wires of the present invention need not have a constant cross-sectional shape or size throughout their length. For example, in one exemplary embodiment, the puller wires are generally circular in cross-section over the length that extends through the proximal section 12 of the catheter body 10, and then flatten out (generally like a boat oar) into a generally rectangular cross-sectional configuration in the tip section 14.

The distal ends of the puller wires are fixedly secured to each other at joint 34c by soldering, welding or any other suitable means. The distal end of the mated puller wire pair need not be anchored in the tip section of the catheter, but may be if desired. If anchored, any conventional technique for anchoring a puller wire in a tip section of a catheter may be used.

Figure 9:
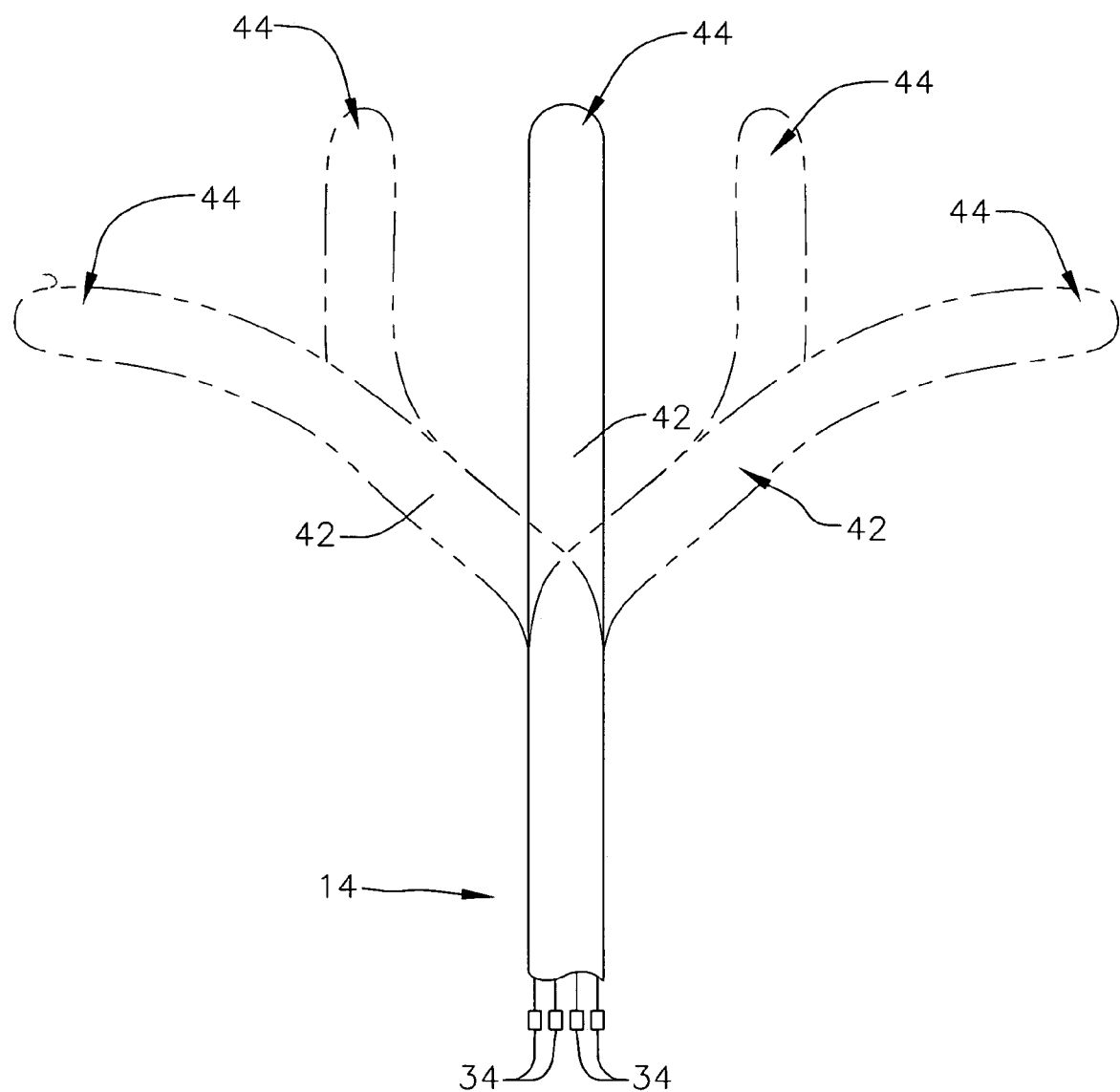
FIG. 9 is a schematic depicting the deflection of the tip section according to an alternative embodiment of the invention.

In another alternative embodiment, as depicted in FIG. 9, two mated pairs of puller wires 34 are provided. The first pair of mated puller wires are secured together at their distal ends, as discussed above, and extend to a first location 44 generally at the distal end of the tip section 14. The second pair of mated puller wires are secured together at their distal ends, as discussed above, and extend to a second position 42 generally at about the midpoint of the tip section 14. The first puller wire pair can be used to deflect the distal end of the tip section 14 in one of two possible opposing directions. The second puller wire pair can be used to deflect the proximal end of the tip section 14 in one of two possible opposing directions. This arrangement allows the tip section to be deflected or bent at two locations. The bends may be in the same direction or in opposite directions as shown in FIG. 9. It is understood that the locations of the distal ends of the puller wire pairs can vary as desired.

The puller wires extend proximally from the catheter body into a suitable control handle where the puller wires may remain adjacent to each other or may be separated, depending on the design of the control handle. Typically, the proximal ends of the puller wires will be connected to structures that can be moved to apply a proximally directed force on one of the puller wires. Longitudinal movement of a puller wire 34 in a proximal direction relative to the catheter body section 12 results in deflection of the tip section 14.

Examples of other suitable control handles that can be used with the present invention are described in U.S. Pat. Nos. 6,123,699, 6,171,277, 6,183,463, and 6,198,974, the disclosures of which are incorporated herein by reference.

It is presently preferred to utilize a control handle that simultaneously applies a force to one puller wire of a puller wire pair in a proximal direction while applying a force to the second puller wire of the puller wire pair, i.e., a handle that pulls one wire and pushes the other wire at the same time. An example of such a handle utilizing a single gear arrangement is described in U.S. Pat. No. 6,468,260 and U.S. Patent Application Ser. No. 60/133,182, the disclosures of which are incorporated herein by reference.

Figure 10:
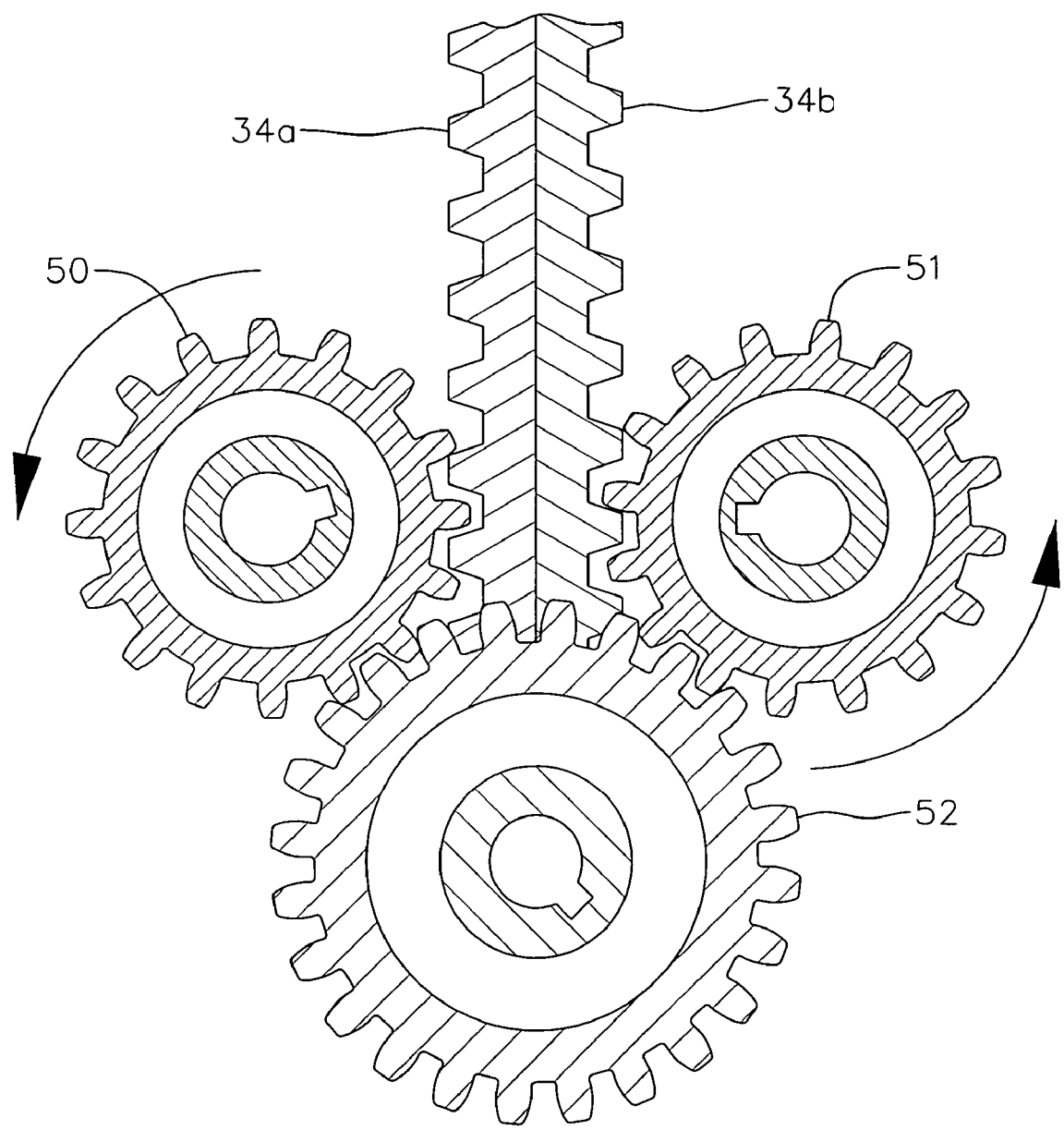
FIG. 10 is a perspective view of a gear arrangement useful for manipulating the puller wires of the invention.

With respect to FIG. 10, there is shown a gear arrangement useful for simultaneous pulling of one puller wire and pushing of the other. In this embodiment, the proximal end portions of each puller wire 34a and 34b comprise a plurality of gear teeth. The puller wire pair extends between first and second gears 50 and 51, each having teeth that engage the teeth of puller wires 34a and 34b respectively. A third gear 52 simultaneously engages the teeth of the first gear 50 and second gear 51 such that rotation of the third gear in one direction, e.g., clockwise, results in rotation of both the first and second gears in the opposite direction, e.g., counter-clockwise. This, in turn, results in longitudinal movement of one puller wire in a proximal direction and the other in a distal direction. Rotation of the third gear can be accomplished by means of a know or handle that is fixably attached to the third gear and extends to the outside of the handle housing where it can be manipulated by an operator.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fairest scope.

What is claimed is:

1. A steerable catheter comprising:
    an elongated tubular catheter body having at least one lumen extending therethrough and a flexible tubular tip section extending from the distal end of the catheter body and having at least one lumen extending therein in communication with a lumen extending through the catheter body;
    a control handle at the proximal end of the catheter body comprising at least one member manually movable between first and second positions;

first and second puller wires extending from the control handle through a lumen in the catheter body and into a lumen in the tip section, said first and second puller wires being attached to each other at their distal ends and being slidably interlocked to resist separation along at least the length of the first and second puller wires that extend through the catheter body and tip section, the proximal end of the first puller wire being coupled to a movable member in the control handle and the proximal end of the second puller wire being coupled to a second movable member or a stationary movable member in the control handle;

whereby movement of the movable member in the control handle coupled to the first puller wire from its first to its second positions results in deflection of the catheter tip.

2. A steerable catheter as claimed in claim 1 wherein each of the puller wires has at least one generally flat surface.

3. A steerable catheter as claimed in claim 1 wherein each of the puller wires has a generally rectangular cross-section.

4. A steerable catheter as claimed in claim 1 wherein the puller wires extend through a tubular sleeve and are maintained in mated relationship by means of the tubular sleeve.

5. A steerable catheter as claimed in claim 4 wherein the sleeve has a generally rectangular or oval cross-sectional shape.

6. A steerable catheter as claimed in claim 1 wherein the puller wires extend through a shaped lumen in the tip section and are maintained in mated relationship by means of the shaped lumen.

7. A steerable catheter as claimed in claim 6 wherein the shaped lumen has a generally rectangular or oval cross-sectional shape.

8. A steerable catheter as claimed in claim 1, wherein the proximal ends of the first and second puller wires are coupled to first and second movable members respectively, each movable members being movable between first and second positions.

9. A steerable catheter as claimed in claim 1 wherein movement of the first movable member from its first position to its second position results in proximal movement of the first puller wire relative to the second puller wire.

10. A steerable catheter as claimed in claim 1 wherein movement of the first movable member from its first position to its second position results in a force being applied to the first puller wire in a proximal direction and a force being applied to the second puller wire in a distal direction.

11. A steerable catheter as claimed in claim 1, wherein the first puller wire comprises at least one notch generally along its length, and the second puller wire comprises at least one rib sized and shaped to slidably interlock with the notch in the first puller wire.

12. A steerable catheter as claimed in claim 11, wherein the first puller wire comprises a plurality of notches generally along its length, and the second puller wire comprises a common plurality of ribs sized and shaped to slidably interlock with the notches on the first puller wire.

13. A steerable catheter as claimed in claim 11, wherein each of the at least one notch and the at least one rib has a generally rectangular cross-sectional shape.

14. A steerable catheter as claimed in claim 11, wherein each of the at least one notch and the at least one rib has a generally round cross-sectional shape.

15. A steerable catheter comprising:

an elongated tubular catheter body having at least one lumen extending therethrough and a flexible tubular tip section extending from the distal end of the catheter body and having at least one lumen extending therein in communication with a lumen extending through the catheter body;

a control handle at the proximal end of the catheter body comprising at least two members manually movable between first and second positions;

first and second puller wire pairs extending from the control handle through a lumen in the catheter body and into a lumen in the tip section, each puller wire pair comprising first and second puller wires wherein the first and second puller wires of each puller wire pair are attached to each other at their distal ends and are slidably interlocked to resist separation along at least the length of the first and second puller wires that extend through the catheter body and tip section, the distal end of the first puller wire pair extending into a lumen in the tip section to a first location and the distal end of the second puller wire pair extending into a lumen in the tip section to a second location distal to the first location, and wherein the proximal end of the first puller wire of each puller wire pair is coupled to a separate movable member in the control handle and the proximal end of the second puller wire of each puller wire pair is coupled to a second movable member or a stationary movable member in the control handle;

whereby movement of the movable member in the control handle coupled to the first puller wire of the first puller wire pair from its first position to its second position results in deflection of the catheter tip at the first location and movement of the movable member in the control handle coupled to the first puller wire of the second puller wire pair from its first position to its second position results in deflection of the catheter tip at the first location.

16. A steerable catheter as claimed in claim 15, wherein the first puller wire of each puller wire pair comprises at least one notch generally along its length, and the second puller wire of each puller wire pair comprises at least one rib sized and shaped to slidably interlock with the notch in the first puller wire.

17. A steerable catheter as claimed in claim 16, wherein the first puller wire of each puller wire pair comprises a plurality of notches generally along its length, and the second puller wire of each puller wire pair comprises a common plurality of ribs sized and shaped to slidably interlock with the notches on the first puller wire.

18. A steerable catheter as claimed in claim 16, wherein each of the at least one notch and the at least one rib has a generally rectangular cross-sectional shape.

19. A steerable catheter as claimed in claim 16, wherein each of the at least one notch and the at least one rib has a generally rectangular cross-sectional shape.

* * * * *

UNITED STATES PATENT AND TRADEMARK OFFICE
CERTIFICATE OF CORRECTION

PATENT NO. : 7,077,823 B2
APPLICATION NO. : 10/716822
DATED : July 18, 2006
INVENTOR(S) : Benjamin D. McDaniel It is certified that error appears in the above-identified patent and that said Letters Patent is hereby corrected as shown below:

Column 7, line 37, Claim 8         Delete "members",
Insert --member--

Column 8, line 56, Claim 19       Delete "rectangular",
Insert --round--

Signed and Sealed this

Seventh Day of August, 2007

JON W. DUDAS
*Director of the United States Patent and Trademark Office*